(12) United States Patent
Mitelberg et al.

(10) Patent No.: US 7,311,726 B2
(45) Date of Patent: *Dec. 25, 2007

(54) INTRAVASCULAR STENT DEVICE

(75) Inventors: Vladimir Mitelberg, Aventura, FL (US); Donald K. Jones, Lauderhill, FL (US)

(73) Assignee: Cordis Neurovascular, Inc., Miami Lakes, FL (US)

( * ) Notice: Subject to any disclaimer, the term of this patent is extended or adjusted under 35 U.S.C. 154(b) by 82 days.

This patent is subject to a terminal disclaimer.

(21) Appl. No.: 11/364,292

(22) Filed: Feb. 28, 2006

(65) Prior Publication Data

US 2006/0149355 A1 Jul. 6, 2006

Related U.S. Application Data

(60) Continuation of application No. 10/743,510, filed on Dec. 22, 2003, now Pat. No. 7,037,331, which is a division of application No. 10/163,248, filed on Jun. 5, 2002, now Pat. No. 6,818,013.

(60) Provisional application No. 60/298,325, filed on Jun. 14, 2001.

(51) Int. Cl.
*A61F 2/06* (2006.01)

(52) U.S. Cl. .................................................. 623/1.15

(58) Field of Classification Search ............... 623/1.11, 623/1.2, 1.15, 1.17, 1.22

See application file for complete search history.

(56) References Cited

U.S. PATENT DOCUMENTS

| 4,443,498 A | 4/1984 | Shinno |
| 4,733,665 A | 3/1988 | Palmaz |
| 4,739,762 A | 4/1988 | Palmaz |
| 4,776,337 A | 10/1988 | Palmaz |
| 5,102,417 A | 4/1992 | Palmaz |
| 5,288,711 A | 2/1994 | Mitchell et al. |
| 5,316,023 A | 5/1994 | Palmaz et al. |
| 5,342,348 A | 8/1994 | Kaplan |
| 5,360,443 A | 11/1994 | Barone et al. |
| 5,516,781 A | 5/1996 | Morris et al. |
| 5,522,880 A | 6/1996 | Barone et al. |
| 5,563,146 A | 10/1996 | Morris et al. |
| 5,571,170 A | 11/1996 | Palmaz et al. |
| 5,571,171 A | 11/1996 | Barone et al. |
| 5,578,071 A | 11/1996 | Parodi |

(Continued)

FOREIGN PATENT DOCUMENTS

EP 1000590 A 8/1999

(Continued)

OTHER PUBLICATIONS

European Search Report (3 pgs.) dated May 12, 2003.

(Continued)

*Primary Examiner*—Bruce Snow
(74) *Attorney, Agent, or Firm*—George H. Gerstman; Seyfarth Shaw LLP

(57) ABSTRACT

A very small diameter intravascular stent device which may be used in balloon angioplasty or in the treatment of an aneurysm in the human brain, which is comprised of a thin-walled skeletal cylindrical tube formed of undulating or sinusoidal elements which, when compressed, nest tightly with each other.

21 Claims, 2 Drawing Sheets

U.S. PATENT DOCUMENTS

| | | |
|---|---|---|
| 5,578,072 A | 11/1996 | Barone et al. |
| 5,646,160 A | 7/1997 | Morris et al. |
| 5,656,023 A | 8/1997 | Caprio, Jr. et al. |
| 5,656,036 A | 8/1997 | Palmaz |
| 5,683,453 A | 11/1997 | Palmaz |
| 5,735,893 A | 4/1998 | Lau et al. |
| 5,741,327 A | 4/1998 | Frantzen |
| 5,807,404 A | 9/1998 | Richter |
| 5,810,872 A | 9/1998 | Kanesaka et al. |
| 5,827,321 A | 10/1998 | Roubin et al. |
| 5,855,600 A | 1/1999 | Alt |
| 5,931,867 A | 8/1999 | Haindl |
| 6,042,597 A | 3/2000 | Kveen et al. |
| 6,083,257 A | 7/2000 | Taylor et al. |
| 6,106,548 A | 8/2000 | Roubin et al. |
| 6,117,165 A | 9/2000 | Becker |
| 6,152,957 A | 11/2000 | Jang |
| 6,179,868 B1 | 1/2001 | Burpee et al. |
| 6,193,747 B1 | 2/2001 | von Oepen |
| 6,267,783 B1 | 7/2001 | Letendre et al. |
| 6,287,336 B1 | 9/2001 | Globerman et al. |
| 6,361,558 B1 | 3/2002 | Hieshima et al. |
| 2003/0004567 A1 | 1/2003 | Boyle et al. |

FOREIGN PATENT DOCUMENTS

| | | |
|---|---|---|
| EP | 1042997 A | 7/2000 |
| EP | 1157673 A | 2/2001 |

OTHER PUBLICATIONS

European Search Report (2 pgs.) dated Nov. 27, 2003.

INTRAVASCULAR STENT DEVICE

This is a continuation of U.S. Application No. 10/743,510, filed Dec. 22, 2003, now U.S. Pat. No. 7,037,331, which is a divisional of U.S. Application No. 10/163,248, filed Jun. 5, 2002, now U.S. Pat. No. 6,818,013, which claims the benefit of provisional patent Application No. 60/298,325, filed Jun. 14, 2001.

BACKGROUND OF THE INVENTION

This invention relates to intravascular devices for implantation within a vessel of the body, and more particularly to a stent device which may be used in the treatment of blood vessel disorders. More specifically, the intravascular device may take the form of an stent device to be used in balloon angioplasty or in the treatment of aneurysms which occur in the brain.

DESCRIPTION OF THE PRIOR ART

On a worldwide basis, nearly one million balloon angioplasties were performed in 1997 to treat vascular disease, including blood vessels clogged or narrowed by a lesion or stenosis. The objective of this procedure is to increase the inner diameter or cross-sectional area of the vessel passage, or lumen, through which blood flows.

Another serious vascular defect is an area of weakened vessel wall that causes a bulge, or bubble, to protrude out in a radial direction from the vessel. This type of defect is called an aneurysm. If untreated, the aneurysm may continue expanding until it bursts thereby causing hemorrhaging from the vessel.

In an effort to prevent restenosis or treat an aneurysm without requiring surgery, short flexible cylinders or scaffolds, made of metal or polymers, are often placed into a vessel to maintain or improve blood flow. Referred to as stents, various types of these devices are widely used for reinforcing diseased blood vessels, for opening occluded blood vessels, and for defining an internal lumen to relieve pressure in an aneurysm. The stents allow blood to flow through the vessels at an improved rate while providing the desired lumen opening or structural integrity lost by the damaged vessels. Some stents are expanded to the proper size by inflating a balloon catheter, referred to as "balloon expandable" stents, while others are designed to elastically resist compression in a "self-expanding" manner.

Balloon expandable stents and self-expanding stents are generally delivered in a cylindrical form, crimped to a smaller diameter and are placed within a vessel using a catheter-based delivery system. When positioned at a desired site within a vessel, these devices are expanded by a balloon, or allowed to "self-expand," to the desired diameter.

One such stent for treatment of abdominal aortic aneurysms is disclosed in U.S. Pat. No. 6,267,783 to Robert P. Letendre, et al. This patent discloses a self-expanding stent which may be used in the treatment of aortic aneurysms. This device may be easily recaptured after placement and repositioned to a new position within the vessel. This patent, assigned to a related company, is subsequently referred to and the disclosure therein is incorporated and made a part of the subject patent application.

Another stent aneurysm treatment device is disclosed in U.S. Pat. No. 6,361,558, assigned to the same assignee as the present application. This patent discloses vasculature stents of various configurations which may be used as stent devices for occluding, or partially occluding, aneurysms located at various positions along the blood vessels.

SUMMARY OF THE INVENTION

There is a need for an improved stent which may be easily delivered to a vasculature site through a very small catheter, is capable of being repositioned and which exhibits sufficient structural integrity and resilience under radial compressive forces. More particularly, there is a need for such a stent that, in its compressed state prior to delivery of the stent, has a diameter which is extremely small. Such a stent could be placed in a very small microcatheter for subsequent positioning within a vessel of the human brain. Obviously, such vessels are extremely small and very tortuous throughout their length.

In accordance with one aspect of the present invention, there is provided a self-expanding stent device which includes a small diameter skeletal tubular member. The skeletal tubular member is comprised of a plurality of cells which are formed by a plurality of generally undulating members and a plurality of struts. The undulating members are generally parallel with the longitudinal axis of the tubular member and are generally parallel to each other. In addition, the undulating members have a plurality of peaks. The undulating members and struts are interconnected and have a repeating pattern in which the proximal ends of the struts are attached to the peaks of the undulating members and the distal end of the struts are attached to the peaks of adjacent undulating members.

In accordance with another aspect of the present invention, the skeletal tubular member has a very small compressed diameter for delivery within a vessel and a normally biased expanded diameter for retaining the stent against the walls of the vessel. As the tubular member is compressed to its small diameter, the peaks of the undulating members pull upon the proximal end of the struts and the distal ends of the struts pull upon peaks of adjacent undulating members thereby causing the cells of the tubular members to collapse and "nest" together. This nesting causes the skeletal tubular member to retain a very small diameter.

In accordance with another aspect of the present invention, the skeletal tubular member includes at least two proximal legs which extend generally parallel to the longitudinal axis of the tubular member and are attached to the proximal end of the tubular member. At least one of the proximal legs includes a T-shaped or I-shaped attachment flange.

In accordance with still another aspect of the present invention, the proximal legs are biased outwardly from the longitudinal axis of the tubular member. The proximal legs preferably include a radiopaque marker for positioning the stent within a vessel.

In accordance with another aspect of the present invention, the tubular member includes at least one distal leg which extends generally parallel to the longitudinal axis of the tubular member and is attached to the distal end of the tubular member. The distal leg preferably includes a radiopaque marker for locating the distal end of the stent as the stent is placed in a vessel.

In accordance with still another aspect of the present invention, there is provided a self-expanding stent device which includes a small diameter skeletal tubular member which is formed with a thin wall. The wall of the tubular member includes a plurality of cells which are formed by a plurality of sinusoidal members and a plurality of struts. The sinusoidal members are generally parallel to the longitudinal axis of the tubular member and are generally parallel to each other. Each sinusoidal member has a plurality of positive peaks and negative peaks. The sinusoidal members and the struts are interconnected and have a repeating pattern in which each strut connects a positive peak of a sinusoidal member with a negative peak of an adjacent sinusoidal member.

In accordance with still anther aspect of the present invention, the skeletal tubular member has a very small compressed diameter for delivery within a vessel and a normally biased expanded diameter for retaining the stent device against the walls of a vessel. As the tubular member is compressed to its small diameter, the positive peaks of the sinusoidal members pull the struts, and the struts pull the negative peaks of adjacent sinusoidal members thereby causing the cells of the tubular member to collapse with the result that the sinusoidal members "nest" together with adjacent sinusoidal members in order to provide a very small diameter stent device.

In accordance with still another aspect of the present invention, a self-expanding stent device is provided which when placed across an aneurysm of a blood vessel reduces, or obstructs, the flow of blood between the aneurysm and its related blood vessel. The stent device includes a small diameter skeletal tubular member which is comprised of a plurality of cells which are formed by a plurality of generally undulating members and a plurality of struts. The undulating members are generally parallel with the longitudinal axis of the tubular member and are generally parallel to each other. In addition, the undulating members have a plurality of peaks. The undulating members and struts are interconnected and have a repeating pattern in which the proximal ends of the struts are attached to the peaks of the undulating members and the distal end of the struts are attached to the peaks of adjacent undulating members.

These and other aspects of the present invention and the advantages thereof will be more clearly understood from the foregoing description in drawings of a preferred embodiment of the present invention.

DESCRIPTION OF THE PREFERRED EMBODIMENT

Figure 1:
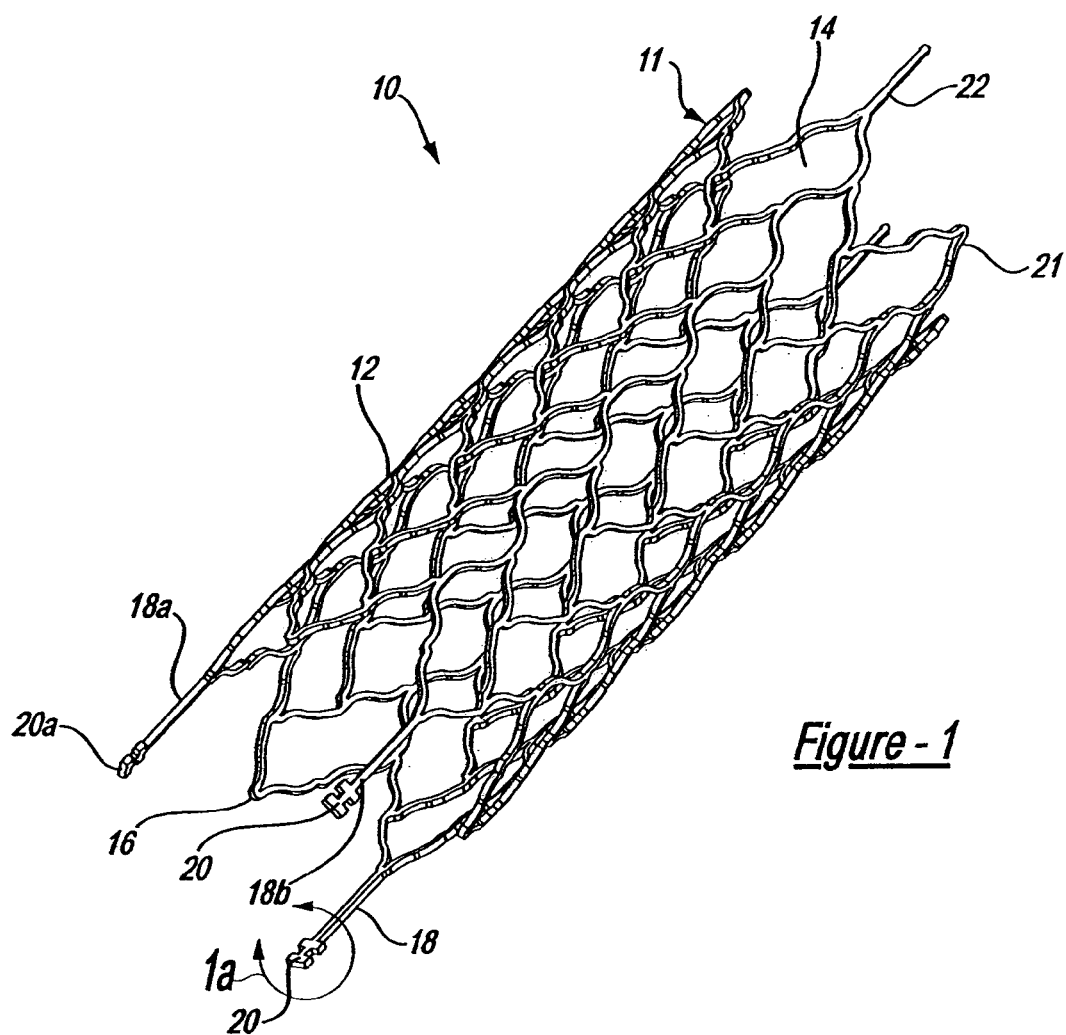
FIG. 1 is an oblique prospective view of an intravascular stent constructed in accordance with a preferred embodiment of the present invention.

FIG. 1 illustrates a self-expanding stent device which is laser cut to form a thin-walled, skeletal tubular member 11 comprised of nickel-titanium alloy. Once cut, the wall of the tubular member 11 includes several openings, or cells 14. When the skeletal tubular member 11 is placed over an aneurysm, a physician is able to deliver embolic coils or other such devices through the cells 14 and into the aneurysm. The tubular member 11 also functions to cover the mouth of the aneurysm thus obstructing, or partially obstructing, the flow of blood into the aneurysm. Also, the tubular member 11 prevents medical devices such as embolic coils from escaping the aneurysm.

The preferred length of the skeletal tubular member 11 may range from 0.0795 inches to 3.15 inches. The diameter of the tubular member 11 varies depending on its deployment configuration. In a non-deployed or expanded state, the diameter of the tubular member 11 may extend up to about 0.4 inches. When the skeletal tubular member 11 is compressed to fit within the lumen of a deployment catheter, the diameter may be reduce to about 0.014 inches.

Attached to the proximal end 16 of the skeletal tubular member 11 are three proximal legs 18, 18a, and 18b that extend longitudinally from the tubular member 11. The proximal legs 18, 18a, and 18b are preferably biased outwardly from the longitudinal axis of the tubular member 11. This outwardly biased configuration aids in the deployment system as subsequently described.

Figure 1A:
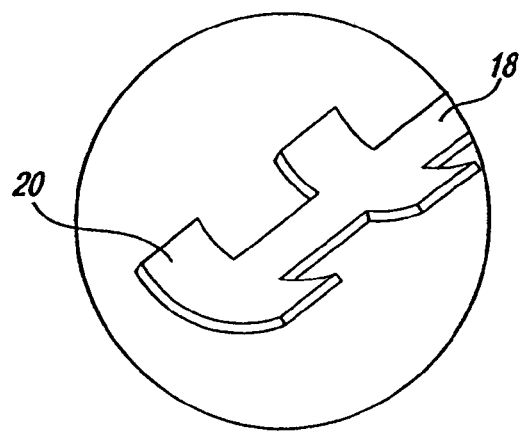
FIG. 1a is an expanded view of the proximal portion of the retaining legs shown in FIG. 1.

T-shaped or I-shaped attachment flanges 20, 20a, and 20b are attached to the tips of each proximal leg 18, 18a, and 18b. FIG. 1a describes the T-shaped or I-shaped flanges 20, 20a, and 20b in more detail. Attached to the distal end 21 of the skeletal tubular member 11 are two distal legs 22 and 22a that extend longitudinally away from the tubular member 11.

FIG. 1a illustrates in detail one of the T-shaped or I-shaped attachment flanges 20 which is also laser cut from the skeletal tubular member 11 at the proximal end of one of the proximal legs 18. The T-shaped or I-shaped attachment flange 20 is slightly arched and oriented on the proximal leg 18 such that the arch coincides with the wall 12 of the tubular member 11.

Figure 2:
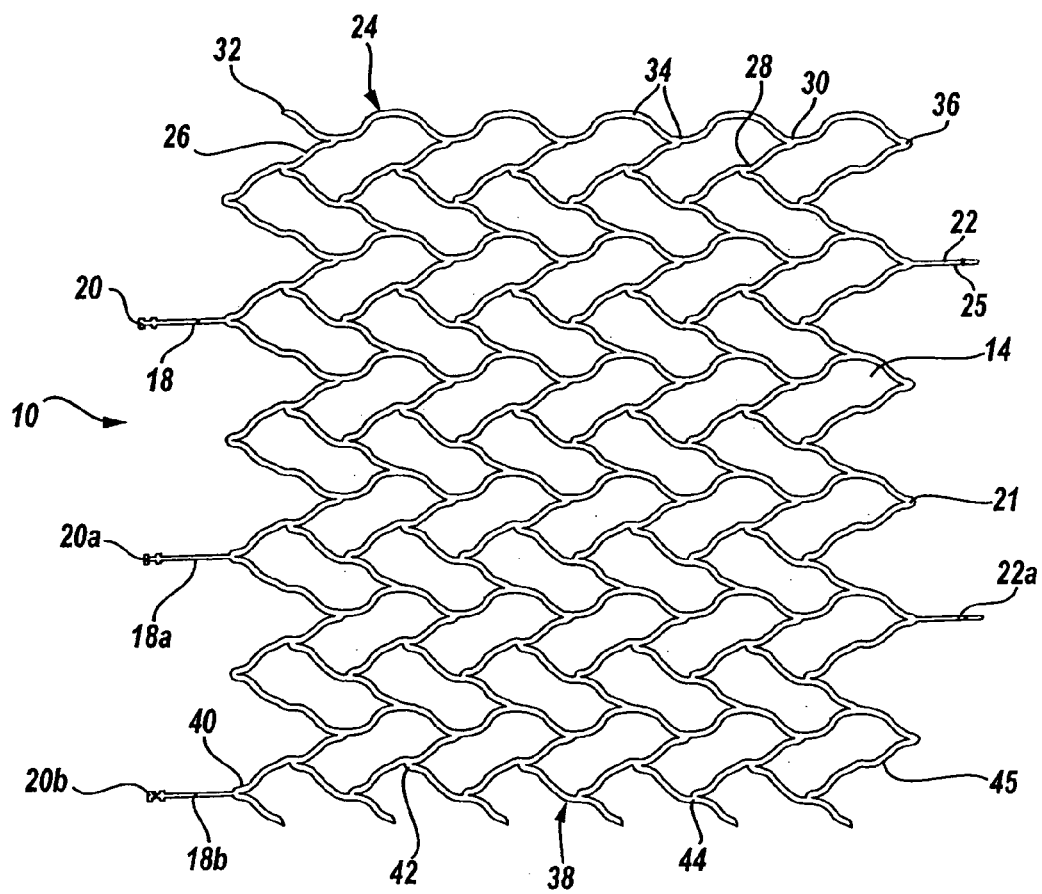
FIG. 2 is a side elevational view of the intravascular stent illustrated in FIG. 1 with the tubular stent being cut along a line and flattened into a single plane; and, FIG. 3 illustrates in more detail the proximal retaining legs of FIG. 1a and the interconnecting elements between the intravascular stent and a positioning catheter.

FIG. 2 illustrates the repetitive cell pattern of the skeletal tubular member 11. The cell pattern may be formed by interconnected undulating members 24 and struts 26. Each strut 26 has a proximal end 28 and a distal end 30. Each undulating member 24 has a proximal end 32, a plurality of peaks 34, and a distal end 36. The proximal end 32 is the left tip of an undulating member 24. The peaks 34 are the highest and lowest points of an undulating member 24. The distal end 36 is the right tip of an undulating member 24.

The undulating members 24 and struts 26 are interconnected in a way to maximize "nesting" of the undulating members 24 to thereby minimize the compressed diameter of the skeletal tubular member 11 during deployment. The proximal end 28 of each strut 26 is attached to a peak 34 of an undulating member 24 and the distal end 30 of the same strut 26 is attached to a peak 34 of an adjacent undulating member 24. This interconnection of undulating members 24 and struts 26 permits the cells 14 of the skeletal tubular member 11 to collapse and allows the tubular member 11 to attain a compressed diameter.

The repetitive cell pattern of the skeletal tubular member 11 may also be formed by interconnected sinusoidal members 38 and struts 26. Each sinusoidal member 38 has a proximal end 40, a plurality of positive peaks 42, a plurality of negative peaks 44, and a distal end 45. The proximal end 40 is the left tip of a sinusoidal member 38. The positive peaks 42 are the highest points of a sinusoidal member 38. The negative peaks 44 are the lowest points of a sinusoidal member 38. The distal end 45 is the right tip of a sinusoidal member 38.

The sinusoidal members 38 and struts 26 are interconnected in a way to maximize "nesting" of the sinusoidal members 38 thereby minimizing the compressed diameter of the skeletal tubular member 11 during deployment. Each strut 26 connects a positive peak 42 of a sinusoidal member 38 with a negative peak 44 of an adjacent sinusoidal member 38. This interconnection of sinusoidal members 38 and struts 26 permits the cells 14 of the skeletal tubular member 11 to collapse and allows the tubular member 11 to attain a compressed diameter.

Also illustrated in FIG. 2 are the proximal legs 18, 18a, and 18b and the distal legs 22 and 22a. In the repetitive cell pattern formed by undulating members 24 and struts 26, the proximal legs 18, 18a, and 18b are connected to the proximal ends 32 of undulating members 24, and the distal legs 22 and 22a are connected to the distal ends 36 of undulating members 24. In the repetitive cell pattern formed by sinusoidal members 38 and struts 26, the proximal legs 18, 18a, and 18b are connected to the proximal ends 40 of sinusoidal members 38, and the distal legs 22 and 22a are connected to the distal ends 45 of sinusoidal members 38.

It should be understood that the stent device of the present invention may alternatively be coated with an agent, such as heparin or rapamycin, to prevent stenosis or restenosis of the vessel. Examples of such coatings are disclosed in U.S. Pat. Nos. 5,288,711; 5,516,781; 5,563,146 and 5,646,160. The disclosures in these patents are incorporated herein by reference.

Figure 3:
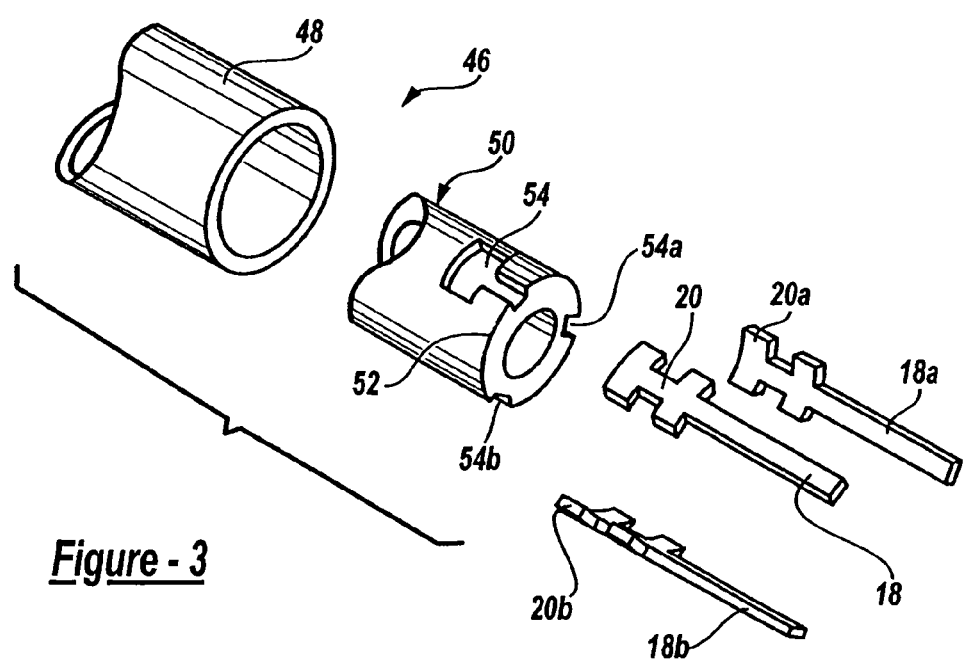

FIG. 3 illustrates the deployment system 46 for the stent device 10. The deployment system 46 includes an outer sheath 48 which is essentially an elongated tubular member, similar to ordinary guiding catheters which are well known to those of ordinary skill in the art. The deployment system 46 also includes an inner shaft 50 located coaxially within the outer sheath 48 prior to deployment. The inner shaft 50 has a distal end 52 and a proximal end (not shown). The distal end 52 of the shaft 50 has three grooves 54, 54a, and 54b disposed thereon. When the deployment system 46 is not fully deployed, the stent device 10 is located within the outer sheath 48. The T-shaped or I-shaped attachment flanges 20, 20a, and 20b on the proximal legs 18, 18a, and 18b of the tubular member 11 are set within the grooves 54, 54a, and 54b of the inner shaft 50, thereby releasably attaching the stent device 10 to the inner shaft 50. This deployment system is described in more detail in U.S. Pat. No. 6,267,783 assigned to the same assignee as the present patent application. The disclosure in this patent is incorporated herein by reference and made a part of the present patent application.

A novel system has been disclosed in which a self-expanding stent device comprises a laser cut, skeletal tubular member having a plurality of cells. Although a preferred embodiment of the invention has been described, it is to be understood that various modifications may be made by those skilled in the art without departing from the scope of the claims which follow.

What is claimed is:

1. A self-expanding stent device comprising:
    a small diameter, skeletal, tubular member having a thin wall and having a proximal end and a distal end;
    said wall of said tubular member comprising a plurality of cells which are formed by a plurality of interconnected, generally undulating members and a plurality of rows of single-strand, unbranched struts;
    said undulating members extending generally in the same direction as the longitudinal axis of said tubular member, said undulating members being generally parallel to each other, forming a plurality of parallel rows;
    each undulating member having a positive peak and a negative peak;
    each strut having a proximal end and a distal end;
    said undulating members and said struts within a row being interconnected and having a repeating pattern in which the ends of said strut are respectively attached to the positive and negative peaks of adjacent undulating members, with adjacent struts extending in the same direction in the same row, and with struts of some rows extending transverse to strands of other rows.

2. The stent device of claim 1 in which each of said undulating members has a plurality of positive peaks and negative peaks arranged in alternating order.

3. A self-expanding stent device as defined in claim 1 in which said skeletal, tubular member has a small, compressed diameter for delivery within a vessel and a normally biased, expanded diameter for retaining said tubular member against the walls of a vessel and arranged whereby, when said skeletal, tubular member is compressed to its small diameter, the positive and negative peaks of said undulating members pull upon the proximal ends of said struts, and the distal ends of said struts pull upon positive and negative peaks of adjacent undulating members, causing said cells of said tubular member to collapse and thereby causing said tubular member to obtain said small diameter.

4. A self-expanding stent device as defined in claim 1, wherein said skeletal, tubular member includes at least two proximal legs, said proximal legs extending generally parallel to the longitudinal axis of said tubular member, and being attached to the proximal end of said skeletal, tubular member, at least one proximal leg including a T-shaped attachment flange.

5. A self-expanding stent device as defined in claim 4, wherein said proximal legs are biased outwardly from the longitudinal axis of said skeletal, tubular member.

6. A self-expanding stent device as defined in claim 4, wherein said proximal legs include a radiopaque marker.

7. A self-expanding stent device as defined in claim 1, wherein said tubular member includes at least one distal leg, said distal leg extending generally parallel to the longitudinal axis of said tubular member and being attached to the distal end of said skeletal, tubular member.

8. A self-expanding stent device as defined in claim 7, wherein said distal leg includes a radiopaque marker.

9. A self-expanding stent device as defined in claim 1, wherein said skeletal, tubular member is constructed from a nickel-titanium alloy.

10. A self-expanding stent device as defined in claim 7, wherein said skeletal, tubular member includes at least two proximal legs, said proximal legs extending generally parallel to the longitudinal axis of said tubular member, and are attached to the proximal end of said skeletal tubular member, at least one proximal end including a T-shaped attachment flange.

11. A self-expanding stent device as defined in claim 10, wherein said proximal legs are biased outwardly from the longitudinal axis of said skeletal, tubular member.

12. A self-expanding stent device as defined in claim 1, in which said stent is constructed for use in the treatment of aneurysms.

13. A self-expanding stent device comprising:
    a small diameter, skeletal tubular member having a thin wall and having a proximal end and a distal end;
    said wall of said tubular member comprised of a plurality of cells which are formed by a plurality of generally undulating members and a plurality of single strand, unbranched struts;
    said struts interconnecting the undulating members, in which said undulating members are generally parallel with the longitudinal axis of said tubular member and are generally parallel to each other
    each undulating member has a positive peak and a negative peak;

each strut has a proximal end and a distal end;

a first undulating member and said struts within a first row have a repeating pattern in which the proximal ends of each of said struts are attached to negative peaks of said undulating member and the distal ends of each of said struts of said first row are attached to positive peaks of a second, adjacent undulating member, and the proximal ends of an adjacent row of struts are attached to positive peaks of said first undulating member;

and the distal ends of each of said struts of said adjacent row are attached to negative peaks of a third, adjacent undulating member;

the struts in each row extending in the same direction in the same row and with the struts of some rows extending transverse to struts of others rows.

14. A self-expandinci stent device as defined in claim 13 in which each of said undulating members has a plurality of positive peaks and negative peaks arranged in alternating order.

15. A self-expanding stent device as defined in claim 13 in which said skeletal, tubular member has a small, compressed diameter for delivery within a vessel and a normally biased, expanded diameter for retaining said tubular member against the walls of a vessel and arranged whereby, when said skeletal, tubular member is compressed to its small diameter, the positive and negative peaks of said undulating members pull upon the proximal ends of said struts, and the distal ends of said struts pull upon positive and negative peaks of adjacent undulating members, causing said cells of said tubular member to collapse and thereby causing said tubular member to obtain said small diameter.

16. A self-expanding stent device as defined in claim 13, wherein said skeletal, tubular member includes at least two proximal legs, said proximal legs extending generally parallel to the longitudinal axis of said tubular member, and being attached to the proximal end of said skeletal, tubular member, at least one proximal leg including a T-shaped attachment flange.

17. A self-expanding stent device as defined in claim 16, wherein said proximal legs are biased outwardly from the longitudinal axis of said skeletal, tubular member.

18. A self-expanding stent device as defined in claim 16, wherein said proximal legs include a radiopaque marker.

19. A self-expanding stent device as defined in claim 13, wherein said tubular member includes at least one distal leg, said distal leg extending generally parallel to the longitudinal axis of said tubular member and being attached to the distal end of said skeletal, tubular member.

20. A self-expanding stent device as defined in claim 19, wherein said distal leg includes a radiopaque marker.

21. A self-expanding stent device as defined in claim 13, wherein said skeletal, tubular member is constructed from a nickel-titanium alloy.

* * * * *